US012629542B2

(12) United States Patent
    Hirvonen

(10) Patent No.: US 12,629,542 B2
(45) Date of Patent: May 19, 2026

(54) TREATMENT PLANNING METHODS AND SYSTEMS THAT CONTROL THE UNIFORMITY OF DOSE DISTRIBUTIONS OF RADIATION TREATMENT FIELDS

(71) Applicant: Siemens Healthineers International AG, Steinhausen (CH)

(72) Inventor: Petri Hirvonen, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 391 days.

(21) Appl. No.: 18/117,943

(22) Filed: Mar. 6, 2023

(65) Prior Publication Data

US 2024/0299772 A1    Sep. 12, 2024

(51) Int. Cl.
    *A61N 5/10*          (2006.01)
(52) U.S. Cl.
    CPC .................................. *A61N 5/1031* (2013.01)
(58) Field of Classification Search
    None
    See application file for complete search history.

(56) References Cited

U.S. PATENT DOCUMENTS 5,647,663 A * 7/1997 Holmes .................. G16Z 99/00
                                                          600/407
2023/0390585 A1* 12/2023 Privalikhin .......... A61N 5/1048

* cited by examiner

*Primary Examiner* — Hoon K Song
(74) *Attorney, Agent, or Firm* — Harness, Dickey & Pierce, P.L.C.

(57)                ABSTRACT

Methods and systems for radiation treatment planning use objective function formulations to evaluate a proposed (candidate) radiation treatment plan, to determine whether or not clinical goals that are specified for treatment of a patient are satisfied by the plan. Dose distributions for a region of a target volume are generated. A value of an objective function formulation is determined. The value of the objective function formulation is a function of difference between a value that is based on a dose distribution and a value for a range that is associated with the treatment field corresponding to the dose distribution. In this manner, the uniformity of doses of individual treatment fields can be controlled. The value of the objective function formulation can be used in a process for optimizing dose distributions in the radiation treatment plan.

21 Claims, 7 Drawing Sheets

800

802
DETERMINE THE MEAN DOSE FOR A DOSE DISTRIBUTION FOR A TREATMENT FIELD IN A REGION

804
DETERMINE AN AVERAGE DOSE OF THE DOSE DISTRIBUTIONS FOR ALL TREATMENT FIELDS THAT INCLUDE THE REGION

806
DEFINE OR ACCESS A RANGE ASSOCIATED WITH THE DOSE DISTRIBUTION

808
EVALUATE THE MEAN DOSE OF THE DOSE DISTRIBUTION AGAINST THE RANGE TO DETERMINE THE VALUE OF THE OBJECTIVE FUNCTION FORMULATION

300

500

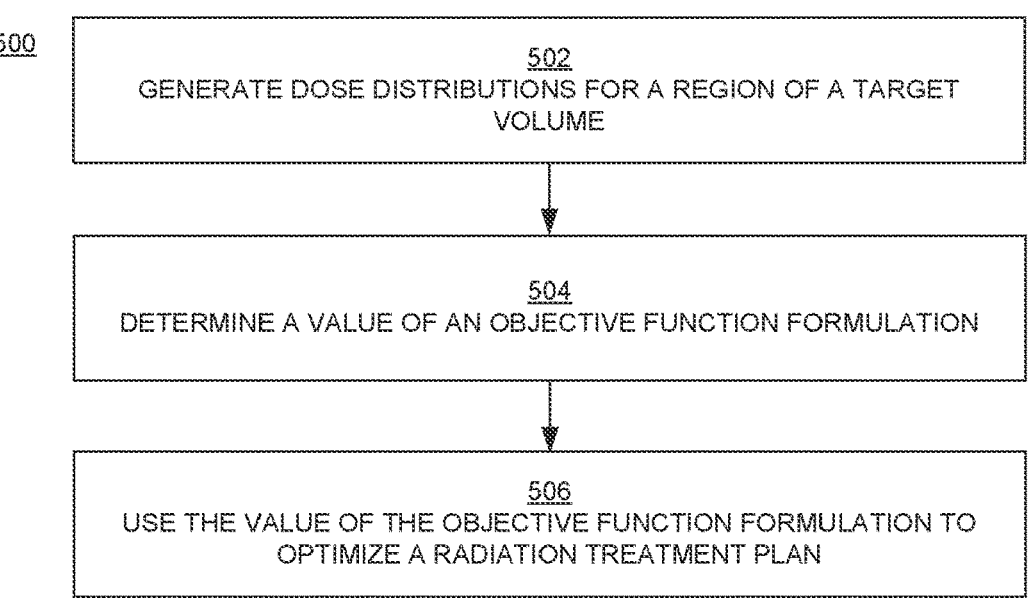

502
GENERATE DOSE DISTRIBUTIONS FOR A REGION OF A TARGET VOLUME

504
DETERMINE A VALUE OF AN OBJECTIVE FUNCTION FORMULATION

506
USE THE VALUE OF THE OBJECTIVE FUNCTION FORMULATION TO OPTIMIZE A RADIATION TREATMENT PLAN

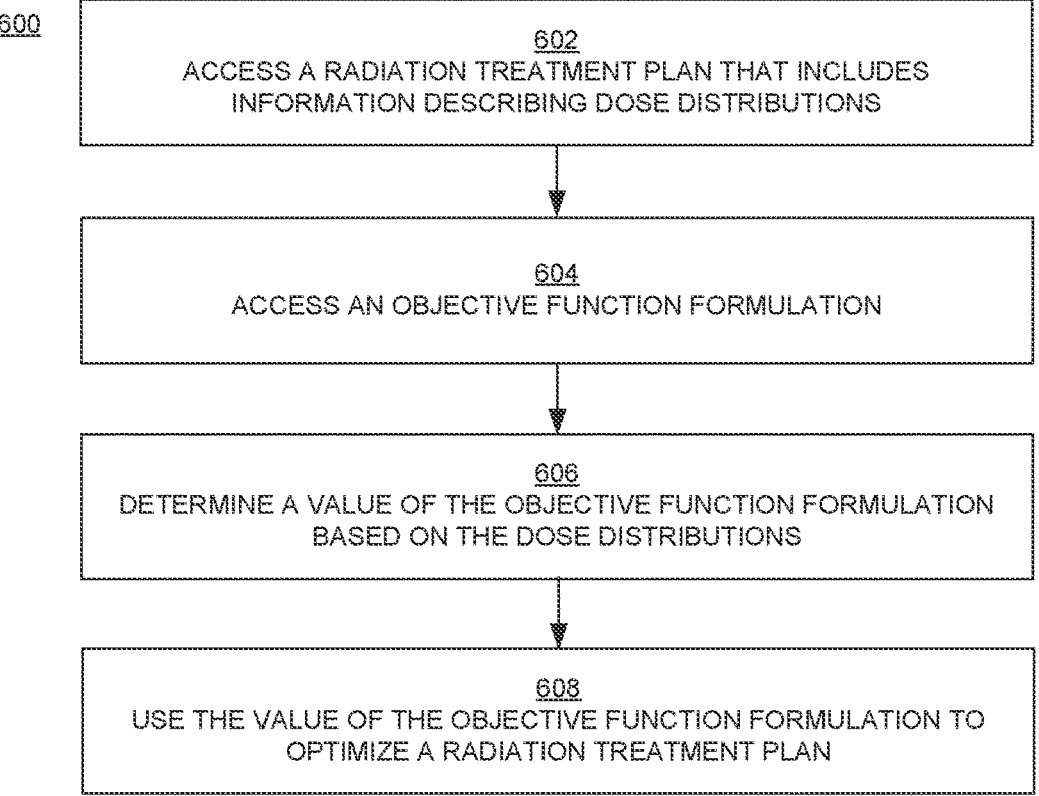

602
ACCESS A RADIATION TREATMENT PLAN THAT INCLUDES INFORMATION DESCRIBING DOSE DISTRIBUTIONS

604
ACCESS AN OBJECTIVE FUNCTION FORMULATION

606
DETERMINE A VALUE OF THE OBJECTIVE FUNCTION FORMULATION BASED ON THE DOSE DISTRIBUTIONS

608
USE THE VALUE OF THE OBJECTIVE FUNCTION FORMULATION TO OPTIMIZE A RADIATION TREATMENT PLAN

Fig. 6

TREATMENT PLANNING METHODS AND SYSTEMS THAT CONTROL THE UNIFORMITY OF DOSE DISTRIBUTIONS OF RADIATION TREATMENT FIELDS

BACKGROUND

The use of radiation therapy to treat cancer is well known. Typically, radiation therapy involves directing a beam of radiation (e.g., a high energy proton, photon, ion, neutron, or electron beam) into a target in the body, such as a malignant tumor, a post-resection tumor bed, a site known to be at risk for tumor progression or a benign lesion, among others.

Radiation therapy using proton beams (proton therapy) has a significant advantage relative to the use of other types of beams. A proton beam reaches a depth in tissue that depends on the energy of the beam, and releases most of its energy (delivers most of its dose) at that depth. The region of a depth-dose curve where most of the energy is released is referred to as the Bragg peak of the beam.

Before a patient is treated with radiation, a treatment plan specific to that patient is developed. The treatment plan defines various aspects of the radiation therapy using simulations and optimizations that may be based on past experiences. In general, the purpose of the treatment plan is to deliver sufficient radiation to the unhealthy tissue while minimizing the exposure of surrounding healthy tissue to that radiation.

During radiation therapy, multiple beams of radiation are directed into the target volume from multiple field angles. The beams are spatially separated from each other; that is, they have different paths through the tissue along which they do not fully overlap with each other, creating a characteristic "peak and valley" dose distribution, and so this type of therapy may be referred to as spatially fractionated radiation therapy (SFRT). Types of spatially separated beams include Grid lattice, minibeam and microbeams, beamlets, pencil beams (spot scanning beams), appropriately oriented and spaced. Radiation therapy can be performed using several radiation treatment modalities, including Intensity Modulated Radiation Therapy (IMRT) and Intensity Modulated Particle Therapy (IMPT).

In IMRT, beams are beams are directed to the target using a collimator. Portions of a beam pass through openings (e.g., holes or slits) in the collimator, while the remaining portions of the beam are blocked or attenuated by the collimator. The openings in the collimator are located so that they are aligned with locations (e.g., spots) in the target volume that are specified in the treatment plan.

In IMPT, beams are focused into the target volume with a collimator and/or with scanning magnets in the nozzle of the treatment machine. In either of those cases, IMPT controls the directions of relatively narrow beams that are directed into locations in the target volume that are specified in the treatment plan.

Thus, during radiation therapy, dose is often delivered from multiple field angles. When optimizing the dose distribution of a multi-field plan, the different treatment fields can be optimized separately or together. In single-field optimization (SFO), the treatment fields are optimized separately and independently of each other. In multi-field optimization (MFO), the treatment fields are optimized together, whereby their total dose is considered in the optimization. In MFO, the dose distributions of individual treatment fields may be inhomogeneous if the sum of the dose distributions satisfies the optimization objectives.

Conceptually speaking, SFO and MFO can be considered as being at opposite ends of a spectrum, each with a varying degree of constraint on the uniformity of the dose distributions of the individual treatment fields. In MFO, there are no constraints in this context, and any field dose is acceptable if the sum of the field doses satisfies the prescription dose. In SFO, the dose of each field is fully constrained to conform to the prescription dose.

SUMMARY

Objective function formulations are used to evaluate a proposed (candidate) radiation treatment plan as part of a process to generate an optimized plan that satisfies clinical goals that are specified for treatment of a patient. Embodiments according to the present disclosure pertain to methodologies that include objective function formulations for optimizing the dose distribution using what is referred to herein as constrained multi-field optimization (CMFO). CMFO can be considered as being somewhere between single-field optimization (SFO) and multi-field optimization (MFO) on the aforementioned spectrum. The CMFO objective function formulations disclosed herein are embodied in new and different methodologies that are applied during radiation treatment planning to control the uniformity of doses of individual treatment fields. CMFO provides users (e.g., treatment planners or clinicians) with intuitive control over the uniformity of the doses of the individual treatment fields.

In embodiments according to the present disclosure, dose distributions for a region of a target volume are generated based on a candidate treatment plan. A value of an objective function formulation is determined. Generally speaking, the value of the objective function formulation is a function of difference between a value that is based on a dose distribution and a value for a range that is associated with the treatment field corresponding to the dose distribution. The value of the objective function formulation can be used in a process for optimizing and thereby controlling dose distributions in the radiation treatment plan.

In an embodiment, a CMFO objective function formulation is a function of the amount that the mean dose of a treatment field deviates from the average dose of two or more or all treatment fields, within the region. In an embodiment, a CMFO objective function formulation is a function of the deviation (e.g., the root mean square deviation, variance, or standard deviation) of dose of a treatment field from the mean dose of the treatment field, within the region. In an embodiment, a CMFO objective function formulation is a function of the deviation of a dose of a treatment field from the mean dose of the treatment field, on a per-voxel basis, within the region; more specifically, this CMFO objective function is a sum over the voxels in the region of the squared deviations of a dose of a treatment field from the mean dose of the treatment field, exceeding a given range. In an embodiment, a CMFO objective function formulation is a function of the deviation of a dose of a treatment field from the smoothed dose of the treatment field, exceeding a given range, on a per-voxel basis, within the region; more specifically, this CMFO objective function is a sum over the voxels in the region of the squared deviations of a dose of the treatment field from the smoothed dose of the treatment field, exceeding a given range. Any number (one or more, including all) of those objective function formulations can be used during treatment planning.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments according to the present disclosure and, together with the detailed description, serve to explain the principles of the disclosure. The drawings are not necessarily drawn to scale.

FIGS. 5 and 6 are flowcharts of examples of computer-implemented methods for radiation treatment planning in embodiments according to the present disclosure.

DETAILED DESCRIPTION

Figure 1:
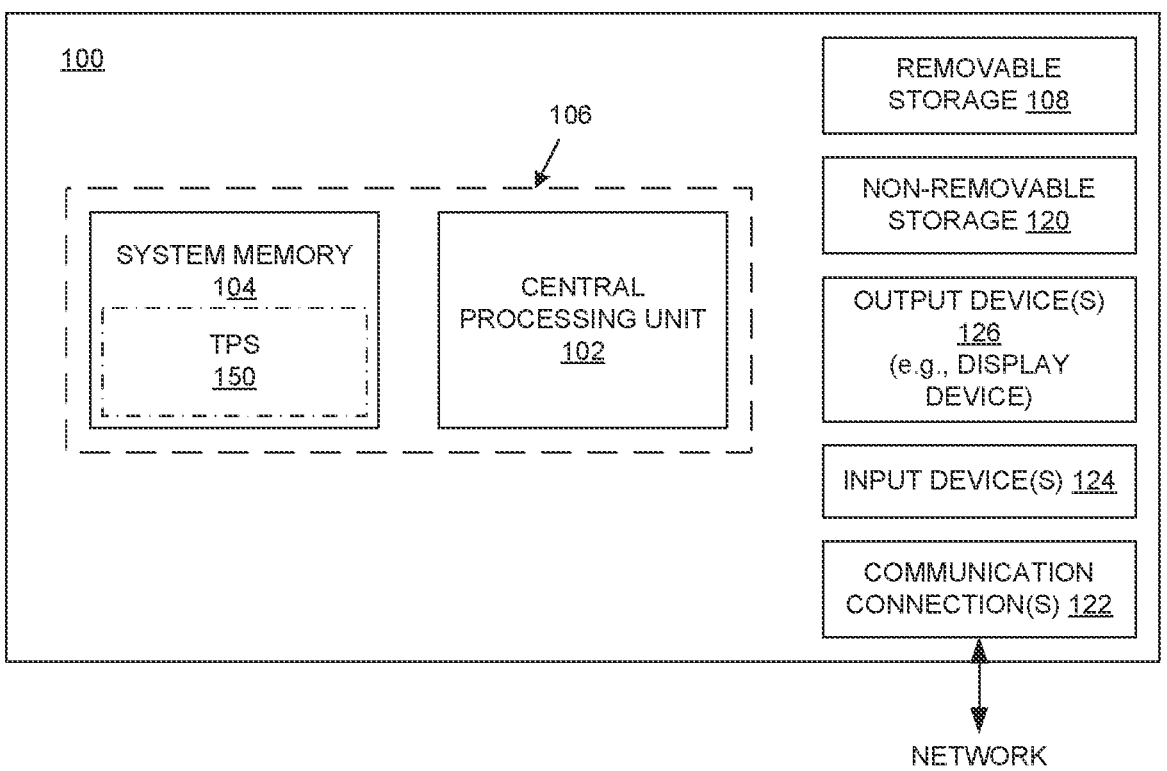
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "determining," "storing," "optimizing," "generating," "evaluating," "using," "selecting," "defining," "summing," "smoothing," "convoluting," "comparing," or the like, refer to actions and processes (e.g., the flowcharts of FIGS. 5, 6, 8, 10, 12, and 14) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

Portions of the detailed description that follows are presented and discussed in terms of methods or processes. Although operations and sequencing thereof are disclosed herein, such operations and sequencing are examples only. Embodiments are well-suited to performing various other operations or variations of the operations described herein.

More specifically, FIGS. 5, 6, 8, 10, 12, and 14 are flowcharts of examples of computer-implemented methods for radiation treatment planning in embodiments according to the present disclosure. The operations of those flowcharts can be implemented as computer-executable instructions (e.g., the treatment planning system 150 of FIG. 1) residing on some form of computer-readable storage medium (e.g., in memory of the computer system 100 of FIG. 1). Also, while the operations in those flowcharts are presented as occurring in series and in a certain order, the present invention is not so limited. The operations may be performed in a different order and/or in parallel, and they may also be performed in an iterative manner to obtain an optimal result.

Embodiments described herein may also be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory, read only memory (ROM), electrically erasable programmable ROM (EE-PROM), flash memory or other memory technology, compact disk ROM (CD-ROM), digital versatile disks (DVDs) or other optical or magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

The discussion to follow may include terms such as "dose," "dose rate," etc. Unless otherwise noted, a value is associated with each such term. For example, a dose has a value and can have different values. For simplicity, each of these terms means its value, unless otherwise noted or apparent from the discussion. Also, the term "deviation" may have its common (layman's) definition (e.g., difference) or it may have its mathematical or statistical definition, depending on its context.

Embodiments according to the present disclosure can be used for radiation therapy/treatment modalities including but not limited to enhanced dose rate (EDR) radiation therapy (RT), ultra-high dose rate (UHDR) RT, and FLASH RT. EDR is defined as a dose rate ranging from one to 40 grays per second (Gy/s). UHDR is defined as a dose rate greater than 40 Gy/s. FLASH RT is a special case of UHDR RT, where in addition to the dose rate, the expected tolerance of the healthy tissue is greater than that expected from low dose rates, due to the so-called "FLASH effect." In particular, embodiments according to the present disclosure include combinations of spatially fractionated radiation therapy (SFRT) including, but not limited to, EDR RT, UHDR RT, and FLASH RT. Embodiments according to the present disclosure are applicable to radiation therapy that delivers any suitable form of radiation in discrete field angles including, but not limited to, protons, photons, ions, neutrons, or electrons. Embodiments according to the present disclosure are applicable to intensity modulated radiation therapy (IMRT) and intensity modulated particle therapy (IMPT).

The methodologies disclosed herein may be useful for stereotactic radiosurgery as well as stereotactic body radiotherapy with single or multiple metastases.

INTRODUCTION

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as a keyboard, mouse, pen, voice input device, touch input device, etc. Output device(s) 126 such as a display device, speakers, printer, etc., may also be included. A display device may be, for example, a cathode ray tube display, a light-emitting diode display, or a liquid crystal display.

In the example of FIG. 1, the memory 104 includes computer-readable instructions, data structures, program modules, and the like associated with a treatment planning system (TPS) 150, which may also be referred to as an optimizer. However, the TPS 150 may instead reside in any one of the computer storage media used by the computer system 100, or may be distributed over some combination of the computer storage media, or may be distributed over some combination of networked computers. The TPS 150 is used to generate and evaluate candidate (proposed) treatment plans and produce a final (optimized) treatment plan. A candidate radiation treatment plan is defined using the TPS 150, stored in a computer system memory, and accessed from that memory.

Figure 4:
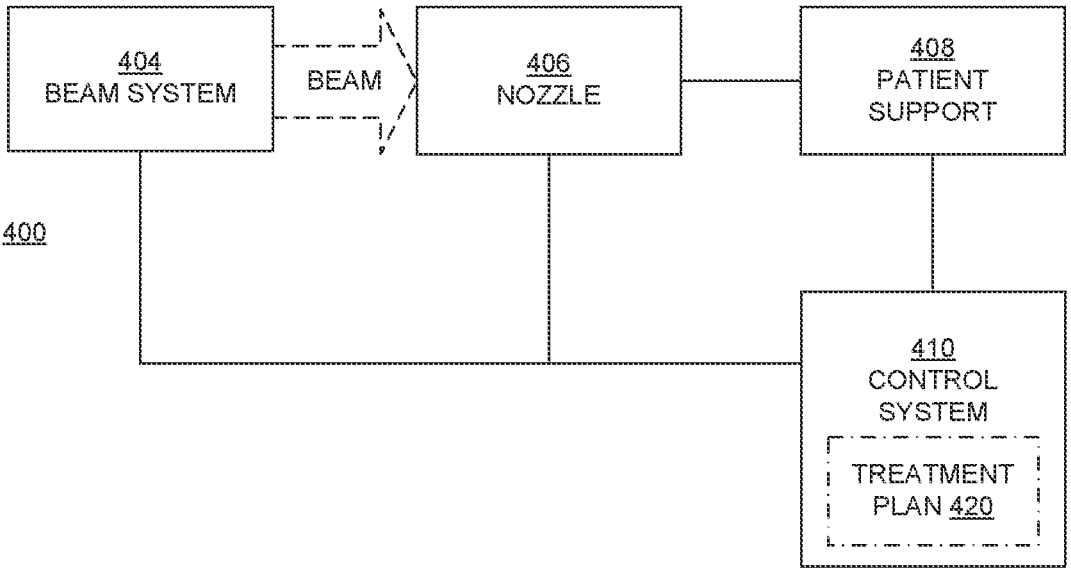
FIG. 4 is a block diagram showing selected components of a radiation therapy system upon which embodiments according to the present disclosure can be implemented.

To deliver the prescribed dose/dose rate of radiation, the radiation treatment plan can be converted (e.g., by the TPS 150) into machine parameters used to configure and control a treatment system (e.g., the system 400 of FIG. 4). Depending on the type of treatment, the machine parameters can include, but are not limited to, beam currents of charged particles, ions, or photon beam intensities, the number of charged particles, ions, or photons per time segment to be emitted by the accelerator, magnet currents, settings to achieve the prescribed energy of beam "particles" (e.g., protons, photons, ions, neutrons, or electrons) at the target volume, and the measurement range of a dose monitor system.

During treatment, in an example embodiment, a beam enters a nozzle of a treatment machine, which may include one or more components that affect (e.g., decrease, modulate) the energy of the beam, to control the dose/dose rate delivered by the beam and/or to control the dose versus depth curve of the beam, depending on the type of beam. For example, for a beam that has a Bragg Peak, the nozzle can control the location of the Bragg Peak in the treatment target laterally to the beam axis.

Examples of Automated Radiation Treatment Planning Processes

A candidate or proposed radiation treatment plan includes values of parameters that can affect dose and/or dose rate, as well as other parameters. The parameters depend on the treatment modality.

The parameters may include, but are not limited to: treatment field (the regions in a patient that will receive radiation); beam shape; beam collimation; number and arrangement of spots; spot weights; beam weights; beam intensities or energies; beam directions; prescribed dose and prescribed dose rate; a number of irradiations of a target volume; a duration of each of the irradiations (irradiation times); and a dose deposited in each of the irradiations. The parameters may also include a period of time during which the irradiations are applied (e.g., a number of irradiations are applied over a period of time such as an hour, with each irradiation in the period of time separated from the next by another period of time; while a treatment session may be relatively long, individual beam delivery times may be less than, even much less than, a second) and an interval of time between each period of irradiations (e.g., each hour-long period is separated from the next by a day).

The large number of parameters and their ranges of values can lead to an effectively infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

Because of the different parameters that need to be considered, the range of values for those parameters, the interrelationship of those parameters, the need for treatment plans to be effective yet minimize risk to the patient, and the need to generate high-quality treatment plans quickly, the use of the treatment planning system 150 executing consistently on the computer system 100 (FIG. 1) for radiation treatment planning as disclosed herein is important.

Figure 2:
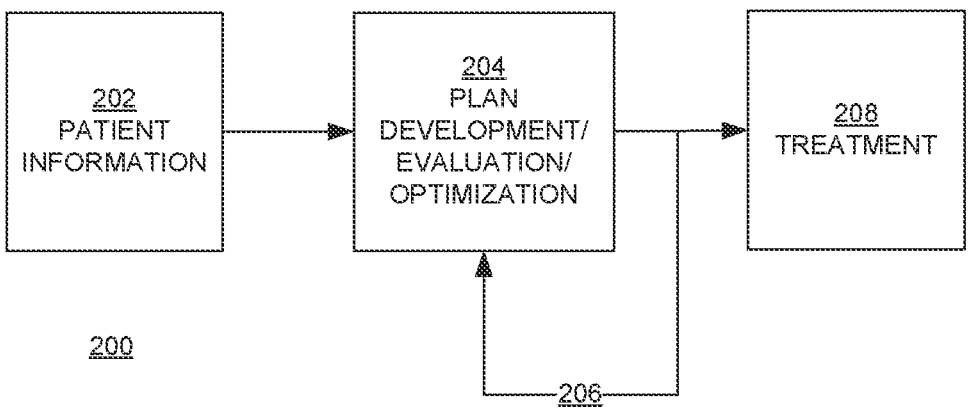
FIGS. 2 and 3 are block diagrams illustrating examples of an automated radiation therapy treatment planning process in embodiments according to the present disclosure.

FIG. 2 is a block diagram illustrating an example of an automated radiation therapy treatment planning process 200 in embodiments according to the present disclosure. The process 200, in whole or in part, may be implemented as a software program, hardware logic, or a combination thereof on/using the computer system 100 (FIG. 1).

In block 202 of FIG. 2, three-dimensional (3D) images of a patient are obtained, and organs and other structures in the patient (the patient geometry) can be segmented and contoured. In blocks 204 and 206, the information from block 202, and other information such as that mentioned above, are used to develop and evaluate a candidate treatment plan, as described further below in conjunction with FIG. 3.

In block 208, if the candidate treatment plan is satisfactory (e.g., it satisfies clinical goals), then the plan may be used for treatment of the patient. If not, then aspects of the treatment plan and/or of the clinical goals may be modified iteratively until a satisfactory plan is generated. The clinical goals may be expressed in terms of, for example, a set of quality metrics, such as dose uniformity in the target volume, conformity to the target volume, critical organ sparing, and the like, with respective target or threshold values for the quality metrics.

In practice, the clinical goals may conflict with each other, in the sense that not all of the clinical goals can be satisfied by any particular treatment plan. Where clinical goals conflict, some or all of the parameter values for each candidate radiation treatment plan can be iteratively adjusted to determine a final set of parameter values for each plan that results in a plan that satisfies the objectives (clinical goals) for treatment of the patient and minimizes the total objective function for that plan. For instance, a dose prediction model (e.g., an element of the TPS 150 of FIG. 1) can be used to generate alternative outcomes for various combinations of the adjustable parameters, and a total objective function can be computed for various alternative outcomes until a minimum or satisfactory value is found, as described further below.

Figure 3:
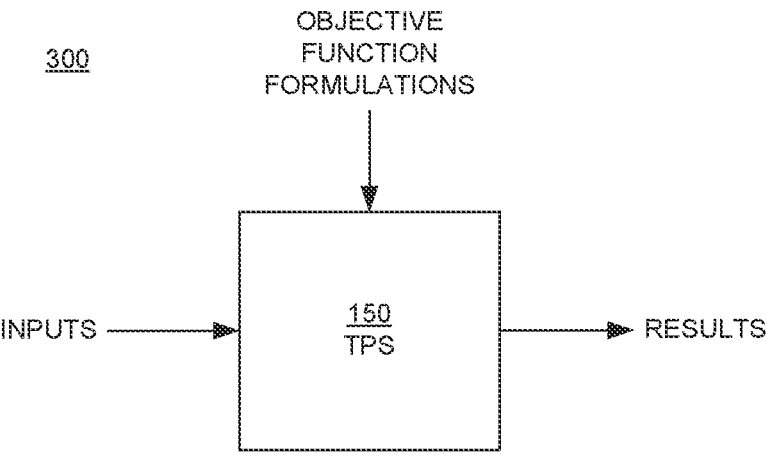

FIG. 3 is a block diagram illustrating an example of an automated radiation therapy treatment planning process 300 in embodiments according to the present disclosure. The process 300, in whole or in part, may be implemented as a software program, hardware logic, or a combination thereof on/using the computer system 100 (FIG. 1). The process 300 corresponds generally to blocks 204 and 206 of FIG. 2.

In the example of FIG. 3, the TPS 150 accesses or receives (e.g., from the memory 104 of FIG. 1) information that includes parameters such as those mentioned above. The TPS 150 can also access or receive information specific to the patient to be treated (e.g., patient geometry), including information that describes a treatment or target volume (or region of interest, ROI), which can include a planned target volume (PTV), gross tumor volume (GTV), clinical target volume (CTV), and organs-at-risk (OARs).

The TPS 150 also accesses or receives objective function formulations (or cost functions) that are defined for the treatment of the patient. Objective function formulations are mathematical formulations of variables (parameters such as those mentioned above) that can have an effect on achieving the clinical goals. More specifically, the objective function formulations are used to evaluate candidate radiation treatment plans, to determine whether or not the clinical goals that are specified for treatment of a patient are satisfied.

In embodiments, the goal is to minimize the value of each objective function formulation. However, in practice, there may be several objective function formulations that are to be minimized in order to achieve an optimal final treatment plan. The objective function formulations may conflict with each other; that is, minimizing the value of one objective function formulation may penalize (e.g., increase) the value of another objective function formulation, and so minimizing the values of all of the objective function formulations may not be achievable. Thus, in embodiments, the objective function formulations are weighted and summed to provide a total of all of the objective function formulations, and that total is then minimized.

In embodiments, a candidate treatment plan that yields a value for the total objective function that is closest to the minimum (relative to other proposed plans) can be identified as an optimized treatment plan. Information about the optimized treatment plan can be presented to the user (e.g., in a display). A planner can iterate on the planning process, e.g., by adjusting the clinical goals. Once a final optimized treatment plan is determined, adjustable treatment machine parameters corresponding to the final optimized treatment plan can be provided in machine-readable form to the radiation treatment system, which can then be operated in accordance with the plan to deliver radiation treatment to a patient.

Example Treatment System

FIG. 4 is a block diagram showing selected components of a radiation therapy or treatment system 400 upon which embodiments according to the present invention can be implemented. In the example of FIG. 4, the system 400 includes a beam system 404 and a nozzle 406.

The beam system 404 generates and transports a beam. In embodiments, depending on the type of beam, the beam system 404 includes components that direct (e.g., bend, steer, focus, or guide) the beam in a direction toward and into a nozzle 406. The beam system 404 may also include components that are used to adjust (e.g., reduce or modulate) the beam energy entering the nozzle 406. The nozzle 406 is used to aim or direct the beam toward various locations or spots in a target volume within a patient supported on the patient support device 408 (e.g., a chair or table) in a treatment room. The nozzle 406 may be mounted on or a part of a gantry that can be moved relative to the patient support device 408, which may also be moveable. The nozzle 406 may also include components that direct the beam and/or adjust the beam energy.

The control system 410 implements a prescribed or optimized or final radiation treatment plan 420 received from the TPS 150 (e.g., see FIG. 1). In embodiments, the control system 410 includes a computer system having a processor, memory, an input device (e.g., a keyboard), and perhaps a display, similar to the system 100 of FIG. 1. The control system 410 can receive data regarding operation of the system 400. The memory of the control system 410 stores the radiation treatment plan 420 that will be implemented using the system 400. Specifically, the memory of the control system 410 includes computer-readable instructions, data structures, program modules, and the like associated with the radiation treatment plan 420. The control system 410 can control parameters of the beam system 404, nozzle 406, and patient support device 408, including parameters such as the energy, intensity, direction, size, and/or shape of the beam, according to data it receives and according to the radiation treatment plan 420.

Radiation Treatment Planning Methods

Embodiments according to the present disclosure introduce new objective function formulations, which may also be referred to as cost functions, for optimizing the dose distribution during treatment planning using what is referred to herein as constrained multi-field optimization (CMFO). Conceptually speaking, CMFO can be considered as being somewhere between single-field optimization (SFO) and multi-field optimization (MFO). The CMFO objective function formulations disclosed herein are embodied in new and different methodologies that are applied during radiation treatment planning to control the uniformity of doses of individual treatment fields. CMFO provides users (e.g., treatment planners or clinicians) with intuitive control over the uniformity of the doses of the individual treatment fields. For example, the CMFO objective function formulations (or a subset thereof) can be used with or added to MFO to achieve CMFO. CMFO provides users (e.g., treatment planners or clinicians) with intuitive control over the uniformity of the individual fields' doses.

In FIGS. 5 and 6, reference is made to the use of objective function formulations in radiation treatment planning in embodiments according to the present disclosure. Embodiments of the CMFO objective function formulations in accordance with the present disclosure are presented and discussed further below in conjunction with FIGS. 7-14. The embodiments and their descriptions of FIGS. 7-14 can be combined (integrated) with the embodiments and their descriptions of FIGS. 5 and 6. The following descriptions pertain to CMFO objective function formulations even if the descriptor "CMFO" is not used, unless otherwise noted. Also, in instances in which a process or operation or the like is described as being performed for a region, treatment field, dose distribution, etc. (singular), the process or operation or the like can be repeated for multiple regions, treatment fields, dose distributions, etc. (plural), either sequentially or in parallel.

With reference first to FIG. 5, in block 502 of the flowchart 500, dose distributions for a region (e.g., a body structure with particular optimization or clinical goals) of a target volume are generated (e.g., based on information in a candidate radiation treatment plan).

In block 504, a value of an objective function formulation is determined (e.g., see FIGS. 7-14).

In embodiments, a value of an objective function formulation for each dose distribution is determined, by evaluating the dose distribution relative to a respective range associated with the dose distribution (e.g., see FIGS. 7-14). In embodiments, each respective range is delineated by a first dose distribution and a second dose distribution. The value of the objective function formulation is non-zero (e.g., greater than zero) when the dose distribution is outside the respective range, and otherwise the value of the objective function formulation is zero. A dose distribution may be entirely outside its range, or only a portion or portions of the dose distribution may be outside its range; in either case, the value of the objective function formulation would be non-zero (e.g., greater than zero).

In block 506, the value of the objective function formulation can be used in a process for optimizing the radiation treatment plan.

In embodiments, as discussed above, optimizing a treatment plan includes determining the minimum value of a total objective function (or cost function) that includes a summation of objective function formulations for that plan, including objective function formulations such as those presented in Equations (1), (2), (3), and (4) that are presented and discussed below. For example, a planner defines a set of quality metrics. For planning, the metrics are defined such that a smaller value is preferred over a larger value. The planner also defines a relative priority or weight for each of the quality metrics. The task of developing an optimal plan is then formulated as a quadratic objective function. The optimal plan is determined by minimizing the total objective function.

With reference next to FIG. 6, in block 602 of the flowchart 600, a radiation treatment plan (e.g., a candidate or proposed plan) that includes information describing dose distributions for a region of a target volume is accessed from computer system memory.

In block 604, an objective function formulation is accessed from computer system memory.

In block 606, a value of the objective function formulation is determined based on the dose distributions (e.g., see FIGS. 7-14).

In block 608, the value of the objective function formulation can be used in a process for optimizing the radiation treatment plan as described above.

CMFO Objective Function Formulations in Radiation Treatment Planning

As noted above, embodiments according to the present disclosure introduce new objective function formulations. In an embodiment, a first objective function formulation is a function of the amount that the mean dose of a treatment field differs from the average dose of all treatment fields, within the region. In an embodiment, a second objective function formulation is a function of the deviation (e.g., the root mean square deviation, variance, or standard deviation) of a dose of a treatment field from the mean dose of the treatment field, within the region. In an embodiment, a third objective function formulation is a function of the deviation of a dose of a treatment field from the mean dose of the treatment field, on a per-voxel basis, within the region. In an embodiment, a fourth objective function formulation is a function of the deviation of a dose of a treatment field from the smoothed dose of the treatment field, exceeding a given range, on a per-voxel basis, within the region. Any number (one or more, including all) of those objective function formulations can be used during treatment planning.

FIGS. 7, 9, 11, and 13 illustrate examples of dose distributions (dose versus position in a target volume). FIGS. 7, 9, 11, and 13 are one-dimensional for ease of illustration; however, the objective function formulations presented herein are applicable to two-dimensional and three-dimensional dose distributions. For example, those formulations can be applied for structures and volumes such as tumors, organs, etc., and the illustrations of FIGS. 7, 9, 11, and 13 are intended only to illustrate how dose distributions across such structures/volumes relate to those formulations. Also, each of those figures includes multiple dose distributions (for example, FIG. 7 includes three dose distributions). The dose distributions shown in any single figure are not necessarily extracted along the same line in a target volume; the dose distributions in any single figure can be along arbitrary lines across the target volume.

Figure 7:
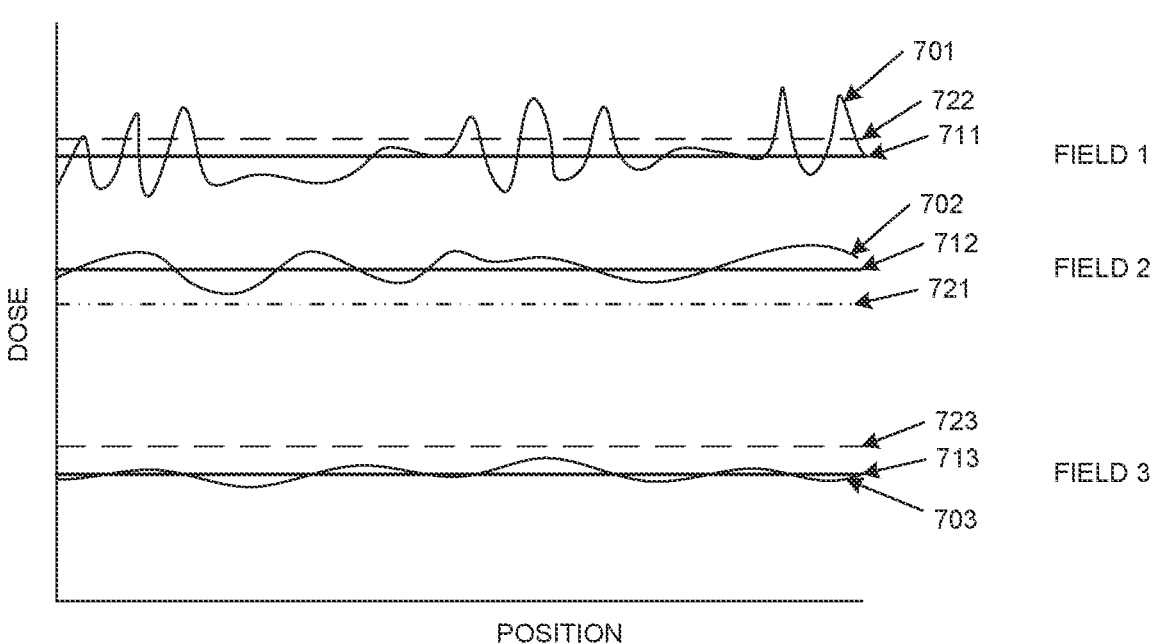
FIGS. 7, 9, 11, and 13 illustrate examples of implementations of objective function formulations in embodiments according to the present disclosure.

With reference to FIG. 7, the first objective function formulation determines a value (a cost value $$C_{rf}^{(1)})$$

that is based on the amount that a mean dose of a treatment field f at a region r of a target volume differs from the average of a set of the treatment fields that include or intersect that region. The set can include at least two of the treatment fields, up to all of the treatment fields, that include or intersect that region. The first objective function formulation is defined as:

$$C_{rf}^{(1)} = w_r w_f \max(0, |\hat{d}_{rf} - \hat{d}_r| - \Delta d_{rf})^2. \qquad (1)$$

In equation (1), $w_r$ and $w_f$ are weighting factors assigned to the region r and the treatment field f, respectively; $\hat{d}_{rf}$ is the mean dose to the region r due to the treatment field f; and $\hat{d}_r$ is the mean dose in the region r averaged over all of the treatment fields that include or intersect that region.

In this embodiment, the mean dose $\hat{d}_{rf}$ can deviate within a given range $\Delta d_{rf}$ that is associated with the region r and treatment field f without penalty (without affecting the value of $$C_{rf}^{(1)}),$$

but outside that range the cost penalty is quadratic. That is if the mean dose $\hat{d}_{rf}$ is outside the range $\Delta d_{rf}$, then the value of $$C_{rf}^{(1)}$$

is non-zero (e.g., greater than zero); otherwise (if the mean dose is not outside that range) the value of $$C_{rf}^{(1)}$$

is zero.

In FIG. 7, the lines 701, 702, and 703 represent examples of dose distributions of three arbitrary treatment fields 1, 2, and 3 within the region r. The dose may be measured in terms of Gy, and the distance or position in terms of millimeters (mm), for example.

The lines 711, 712, and 713 represent the mean doses of the dose distributions 701, 702, and 703, respectively. The line 721 represents the average dose over all three of the treatment fields. The lines 722 and 723 delineate the range associated with the dose distributions 701, 702, and 703. In this example and in the other examples presented below, each range associated with a dose distribution is delineated by a first dose distribution (e.g., the distribution 722) and a second dose distribution (e.g., the distribution 723). In the example of FIG. 7, each of the dose distributions 701, 702, and 703 is associated with the same range; in other examples, the present disclosure is not so limited. In general, a respective range is associated with each dose distribution.

In the example of FIG. 7, the mean doses 711 and 712 of treatment fields 1 and 2 are within the range delineated by the lines 722 and 723 and so they are not penalized, whereas the mean 713 of treatment field 3 is outside that range and so it is penalized during treatment planning with an associated cost according to equation (1).

Figure 8:
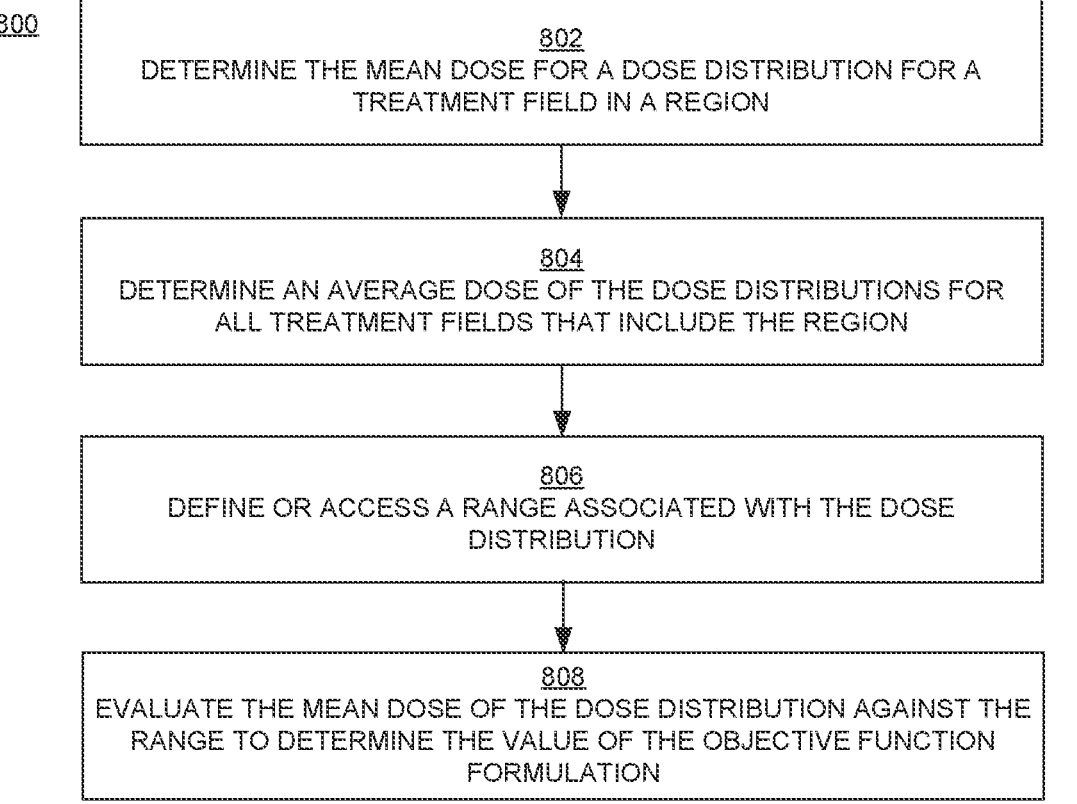
FIGS. 8, 10, 12, and 14 are flowcharts of examples of methods of implementing objective function formulations in embodiments according to the present disclosure.

FIG. 8 is a flowchart 800 of an example of a method for using the first objective function formulation (equation (1)) in embodiments according to the present disclosure. In block 802, the mean dose for a dose distribution for a treatment field in a region is determined.

In block 804, an average dose of the dose distributions for all of the treatment fields that intersect (or include) the region is determined.

In block 806, in an embodiment, a range that is associated with the dose distribution is defined using the average dose (e.g., the range is defined relative to the average dose, to bound the average dose with a margin deemed to be acceptable). In another embodiment, the range is predefined (e.g., as a user input).

In block 808, the mean dose of the dose distribution is evaluated relative to the range associated with the dose distribution, to determine the value of the first objective function formulation.

Figure 9:
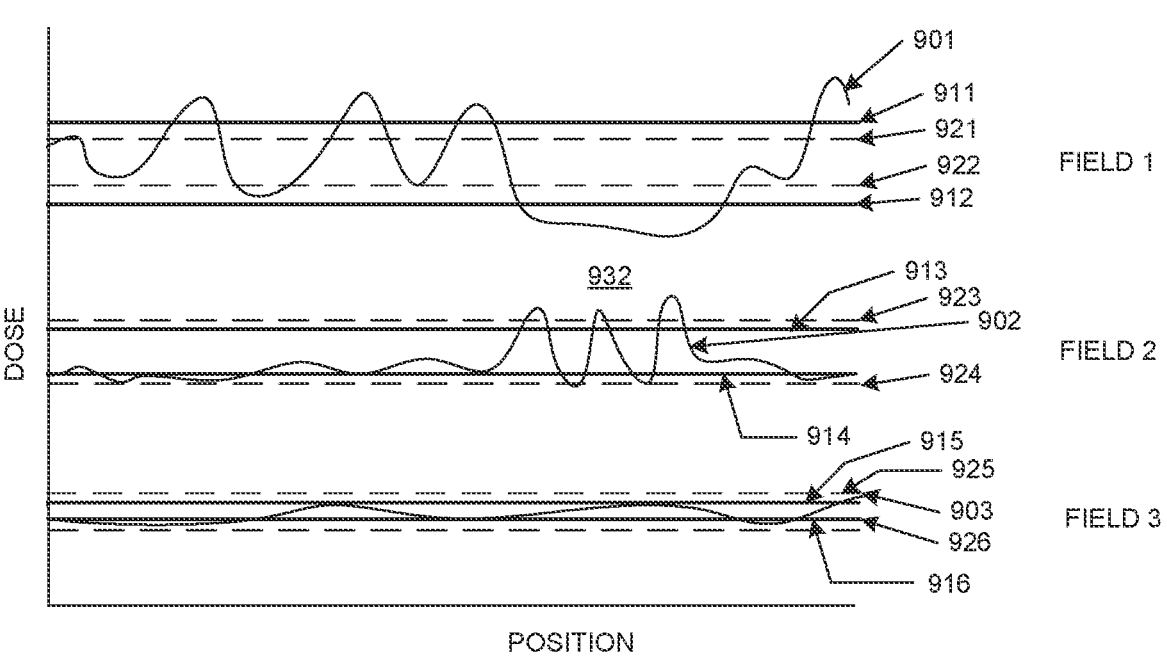

With reference now to FIG. 9, the second objective function formulation determines a value (a cost value $$C_{rf}^{(2)})$$

that is based on deviation of the dose of a treatment field f in a region r of a target volume. The second objective function formulation is defined as:

$$C_{rf}^{(2)} = w_r w_f \max(0, \ R_{rf} - \Delta R_{rf})^2, \ R_{rf} = \sqrt{\frac{\sum_{v \in r} (d_{fv} - \hat{d}_{rf})^2}{\sum_{v \in r} 1}}. \qquad (2)$$

In equation (2), $w_r$ and $w_f$ are weighting factors assigned to the region r and the treatment field f, respectively; $R_{rf}$ is the root mean square deviation of dose from the mean dose $\hat{d}_{rf}$ to the region r due to the treatment field f; and $d_{fv}$ is the dose in a voxel v in the region r. Equation (2) and the discussion below use root mean square deviation as an example of $R_{rf}$. Measures other than the root mean square deviation can be used, such as but not limited to variance or standard deviation.

In this embodiment, deviation (e.g., the root mean square deviation) of dose from the mean dose $R_{rf}$ can vary within a given range $\Delta R_{rf}$ that is associated with the region r and treatment field f without penalty (without affecting the value of $$C_{rf}^{(2)}),$$

but outside that range the cost penalty is quadratic. That is, if the deviation $R_{rf}$ is outside the range $\Delta R_{rf}$, then the value of $$C_{rf}^{(2)}$$

is non-zero (e.g., greater than zero); otherwise (if the deviation $R_{rf}$ is not outside that range) the value of $$C_{rf}^{(2)}$$

is zero.

In FIG. 9, the lines 901, 902, and 903 represent examples of dose distributions of three arbitrary treatment fields 1, 2, and 3 within the region r.

The lines 911 and 912 represent deviation (in the example of FIG. 9, the root mean square deviation is used) of the dose distribution 901; the lines 913 and 914 represent the root mean square deviation of the dose distribution 902; and the lines 915 and 916 represent the root mean square deviation of the dose distribution 903. The lines 921 and 922 delineate the range associated with the dose distribution 901; the lines 923 and 924 delineate the range associated with the dose distribution 902; and the lines 925 and 926 delineate the range associated with the dose distribution 903. Each of those ranges may be predefined or defined in some other manner, and each range can be defined independently of the other ranges (in other words, the ranges may be different).

In the example of FIG. 9, the root mean square deviation of the dose distribution 901 (treatment field 1) is outside the range and so it is penalized during treatment planning with an associated cost according to equation (2). In the example of FIG. 9, the dose distribution 902 (treatment field 2) has greater local variance around a certain position 932 and is outside the associated range at that position, but overall its root mean square deviation is within the range, and so it is not penalized. The root mean square deviation of the dose distribution 903 (treatment field 3) is within the range and so it is not penalized.

Figure 10:
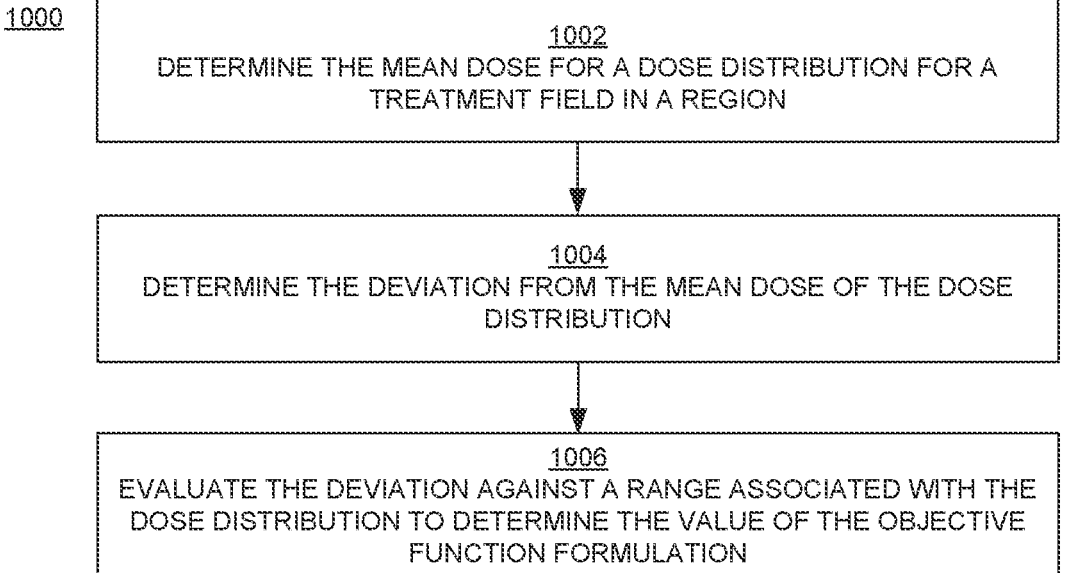

FIG. 10 is a flowchart 1000 of an example of a method for using the second objective function formulation (equation (2)) in embodiments according to the present disclosure. In block 1002, the mean dose for a dose distribution for a treatment field in a region is determined.

In block 1004, deviation (e.g., the root mean square deviation, variance, standard deviation, or the like), from the mean dose, of the dose distribution is determined.

In block 1006, deviation of the dose distribution is evaluated relative to a range associated with the dose distribution, to determine the value of the second objective function formulation.

Figure 11:
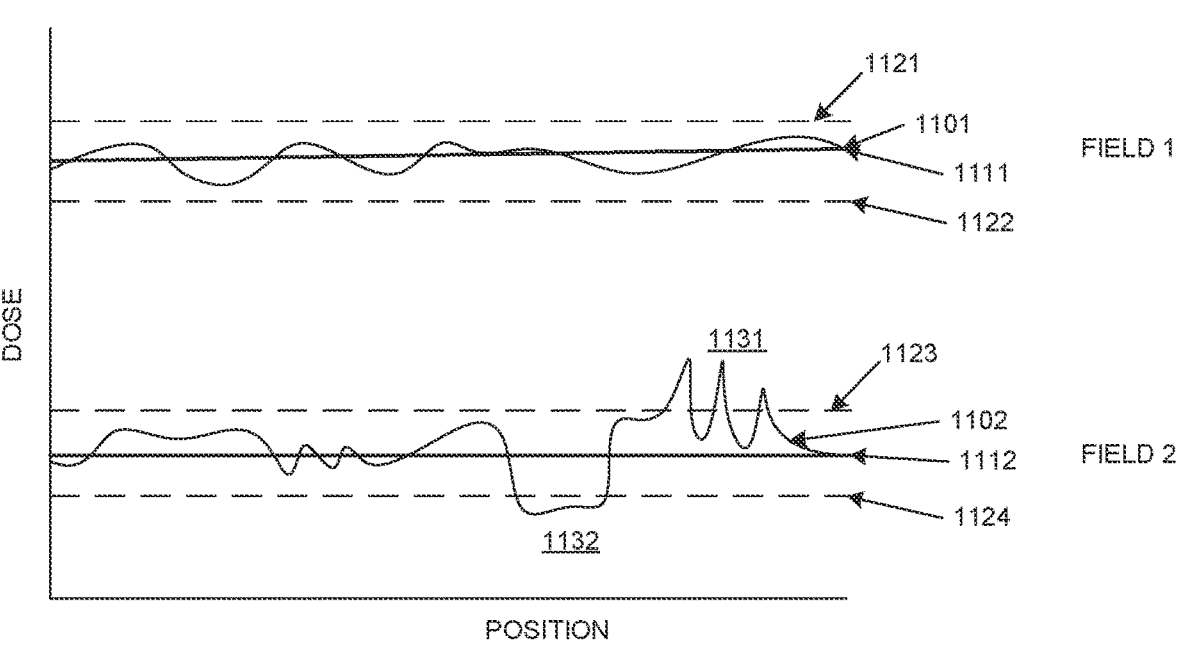

With reference now to FIG. 11, the third objective function formulation determines a value (a cost value $$C_{rf}^{(3)})$$

that is based on deviation of the dose of a treatment field f in a region r of a target volume. More specifically, in an embodiment, the third objective function is a sum over the voxels in the region of the squared deviations of a dose of a treatment field from the mean dose of the treatment field, exceeding a given range. The third objective function formulation is defined as:

$$C_{rf}^{(3)} = \frac{w_r w_f}{\sum_{v \in r} 1} \sum_{v \in r} \max\left(0, |d_{fv} - \hat{d}_{rf}| - \Delta d_{rf}\right)^2. \quad (3)$$

In equation (3), $w_r$ and $w_f$ are weighting factors assigned to the region r and the treatment field f, respectively; $\hat{d}_{rf}$ is the mean dose to the region r due to the treatment field f; and $d_{fv}$ is the dose in a voxel v in the region r.

In this embodiment, the dose $d_{fv}$ in a voxel v can deviate from the mean dose $\hat{d}_{rf}$ to the region r due to the treatment field f within a given range $\Delta d_{rf}$ without penalty (without affecting the value of $$C_{rf}^{(3)}),$$

but outside that range the cost penalty is quadratic. That is, if the difference between the voxel dose $d_{fv}$ and the mean dose $\hat{d}_{rf}$ is outside the range $\Delta d_{rf}$, then the value of $$C_{rf}^{(3)}$$

is increased by a non-zero amount (e.g., greater than zero); otherwise (if the difference is not outside the range $\Delta d_{rf}$) the value of $$C_{rf}^{(3)}$$

is not increased. Per equation (3), the amount of the penalty is determined for each voxel, and then the amounts are summed to determine the value of $$C_{rf}^{(3)}.$$

In FIG. 11, the lines 1101 and 1102 represent examples of dose distributions of two arbitrary treatment fields 1 and 2 within the region r. In this example, a position along the x-axis corresponds to a voxel.

The lines 1111 and 1112 represent the mean doses of the dose distributions 1101 and 1102, respectively. The lines 1121 and 1122 delineate the range associated with the dose distribution 1101, and the lines 1123 and 1124 delineate the range associated with the dose distribution 1102. The ranges may be predefined or defined in some other manner.

In the example of FIG. 11, deviation between the per-voxel dose and the mean dose for the dose distribution 1101 (treatment field 1) is within the range and so it is not penalized. Deviation between the per-voxel dose and the mean dose for the dose distribution 1102 (treatment field 2) is outside the range at the voxel positions 1131 and 1132, and so a penalty is applied for these positions during treatment planning with an associated cost according to equation (3). That is, per equation (3), the amount of the penalty is determined for each voxel, and then the amounts are summed to determine the value of $$C_{rf}^{(3)}.$$

Thus, in this embodiment, the penalty is non-zero (e.g., greater than zero) only for positions where the difference between a voxel dose and the mean dose are outside the range (e.g., at the voxels/positions 1131 and 1132), and the penalty is zero at the other positions on the dose distribution. Accordingly, the value of $$C_{rf}^{(3)}$$

will be non-zero (e.g., greater than zero) if any voxel is outside the range; otherwise (if no voxels/positions are outside the range), the value of $$C_{rf}^{(3)}$$

is zero.

Figure 12:
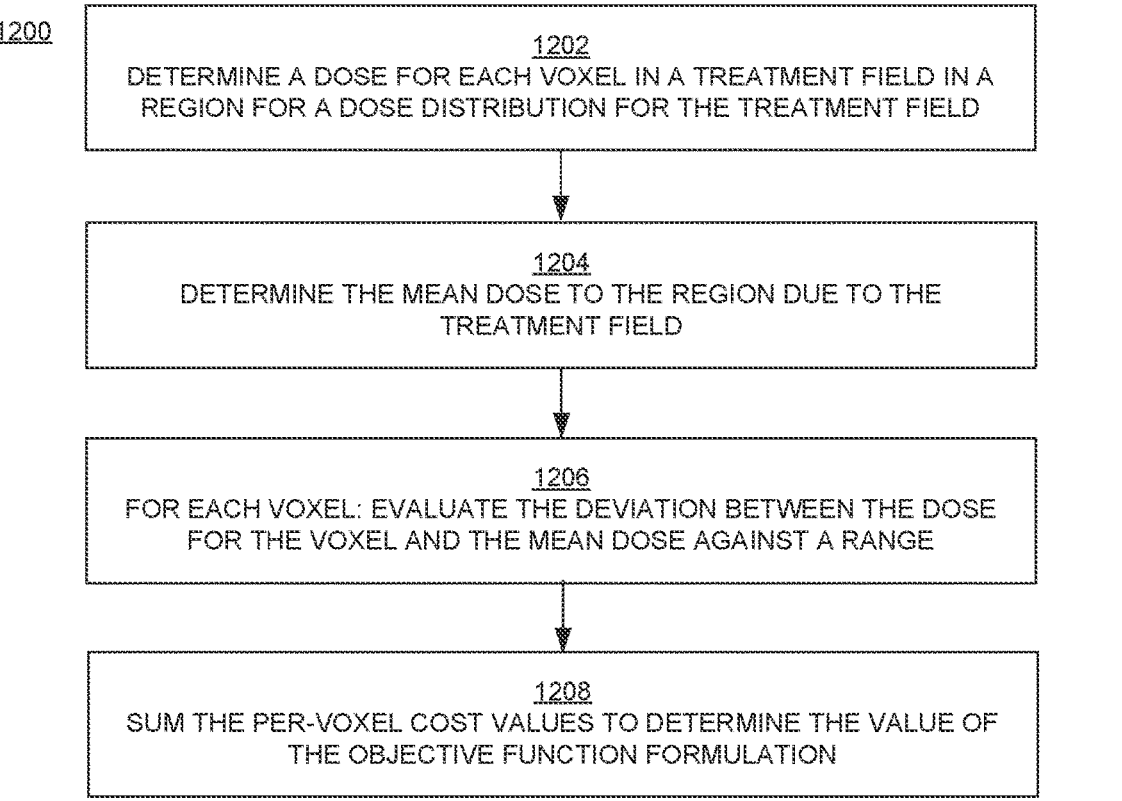

FIG. 12 is a flowchart 1200 of an example of a method for using the third objective function formulation (equation (3)) in embodiments according to the present disclosure. In block 1202, a respective dose value for each voxel in a treatment field in a region is determined using the dose distribution for that treatment field.

In block 1204, the mean dose to the region due to the treatment field is determined.

In block 1206, for each voxel: deviation between the respective dose value for a voxel and the mean dose is evaluated relative to a range associated with the dose distribution to determine a respective per-voxel value for the voxel, where the respective per-voxel value is non-zero (e.g., greater than zero) when the variance for the voxel is outside the range and is zero otherwise.

In block 1208, the per-voxel values are summed to determine the value of the third objective function formulation.

Figure 13:
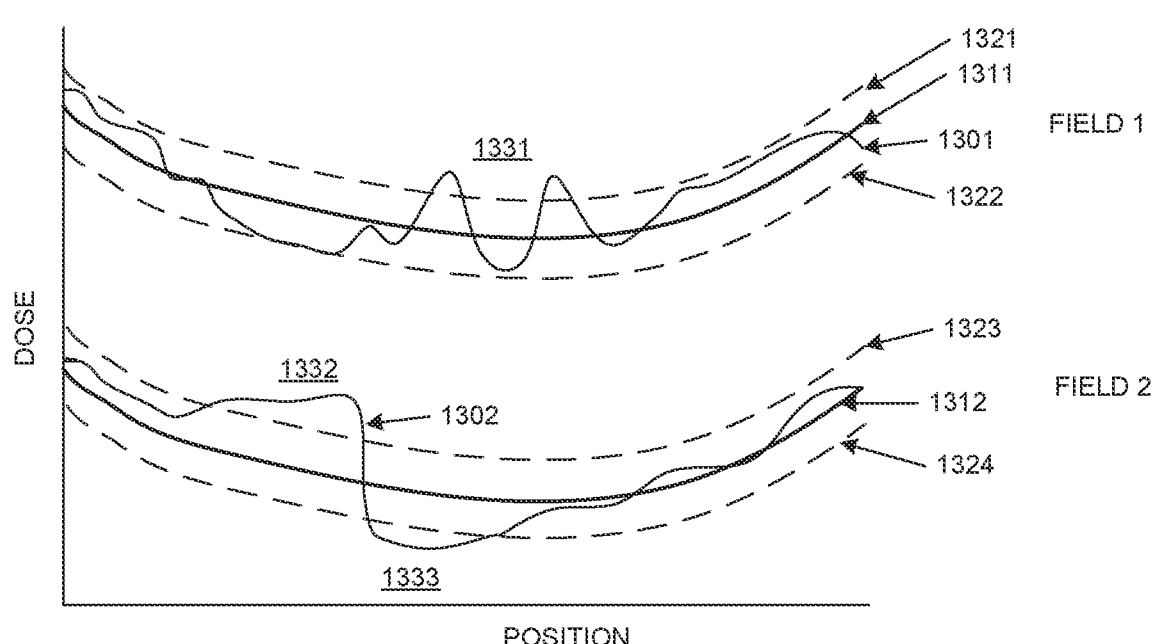

With reference now to FIG. 13, the fourth objective function formulation determines a value (a cost value $$C_{rf}^{(4)})$$

that is based on deviation of the dose of a treatment field f in a region r of a target volume. More specifically, in an embodiment, the fourth objective function is a sum over the voxels in the region of the squared deviations of a dose of the treatment field from the smoothed dose of the treatment field, exceeding a given range. The fourth objective function formulation is defined as:

$$C_{rf}^{(4)} = \frac{w_r w_f}{\sum_{v \in r} 1} \sum_{v \in r} \max(0, |d_{fv} - \partial_{fv}| - \Delta d_{rf})^2, \partial_{fv} = G(\sigma_{rf}) * d_{fv}. \quad (4)$$

In equation (4), $w_r$ and $w_f$ are weighting factors assigned to the region r and the treatment field f, respectively; and $d_{fv}$ is the dose in a voxel v in the region r. In an embodiment, G is a normalized Gaussian kernel, $\emptyset_{rf}$ is the smoothing scale, and * denotes a convolution. The convolution can be computed efficiently using fast Fourier transforms, for example. Smoothing kernels other than a Gaussian kernel or other smoothing techniques can be used.

The fourth objective function formulation provides control over both the local and the large-scale deviation of a field dose within a region. For example, sharp, localized hot- and cold-spots can be penalized while the dose is free to vary smoothly between different parts of the region. Also, abrupt steps in the dose distribution (which can be dangerous with position uncertainties) can be avoided.

In this embodiment, the dose $d_{fv}$ in a voxel v can deviate within a given range $\Delta d_{rf}$ from the smoothed dose $\partial_{fv}$ to the region r due to the treatment field f without penalty (without affecting the value of $$C_{rf}^{(4)}),$$

but outside that range the cost penalty is quadratic. That is, if the deviation between the voxel dose $d_{fv}$ and the smoothed dose $\partial_{fv}$ is outside the range $\Delta d_{rf}$, then the value of $$C_{rf}^{(4)}$$

is increased by a non-zero amount (e.g., greater than zero); otherwise (if that deviation is not outside the range $\Delta d_{rf}$) the value of $$C_{rf}^{(4)}$$

is not increased. Per equation (4), the amount of the penalty is determined for each voxel, and then the amounts are summed to determine the value of $$C_{rf}^{(4)}.$$

In FIG. 13, the lines 1301 and 1302 represent examples of dose distributions of two arbitrary treatment fields 1 and 2 within the region r. In this example, a position along the x-axis corresponds to a voxel.

The lines 1311 and 1312 represent the smoothed doses (with a certain smoothing length scale) of the dose distributions 1301 and 1302, respectively. The lines 1321 and 1322 delineate the range associated with the dose distribution 1301, and the lines 1323 and 1324 delineate the range associated with the dose distribution 1302. The ranges may be predefined or defined in some other manner.

As mentioned above, per equation (4), the amount of the penalty is determined for each voxel, and then the amounts are summed to determine the value of $$C_{rf}^{(4)}.$$

Thus, in this embodiment, the penalty is non-zero (e.g., greater than zero) only where the difference between a voxel dose and the smoothed dose are outside the range.

In the example of FIG. 13, deviation between the per-voxel dose and the smoothed dose for the dose distribution 1301 (treatment field 1) is outside the range at the voxel positions 1331, and so a penalty is applied for these positions during treatment planning with an associated cost according to equation (4). Similarly, deviation between the per-voxel dose and the smoothed dose for the dose distribution 1302 (treatment field 2) is outside the range at the voxel positions 1332 and 1333, and so a penalty is applied for these positions with an associated cost according to equation (4). That is, per equation (4), the amount of the penalty is determined for each voxel, and then the amounts are summed to determine the value of $$c_{\tau f}^{(4)}.$$

Thus, in this embodiment, the penalty is non-zero (e.g., greater than zero) only where deviation between a voxel dose and the mean dose are outside the range (e.g., at the voxels/positions 1331, 1332, and 1333), and otherwise the penalty is zero. Accordingly, the value of $$C_{rf}^{(4)}$$

will be non-zero (e.g., greater than zero) if any voxel/position is outside the range; otherwise (if no voxels/positions are outside the range), the value of $$C_{rf}^{(4)}$$

is zero.

Note that, at the voxels/positions 1332 and 1333, there are relatively abrupt steps in the dose distribution 1302. Such abrupt steps can be dangerous with position uncertainties during treatment. The fourth objective function formulation (equation (4)) mitigates, avoids or precludes such abrupt steps.

Figure 14:
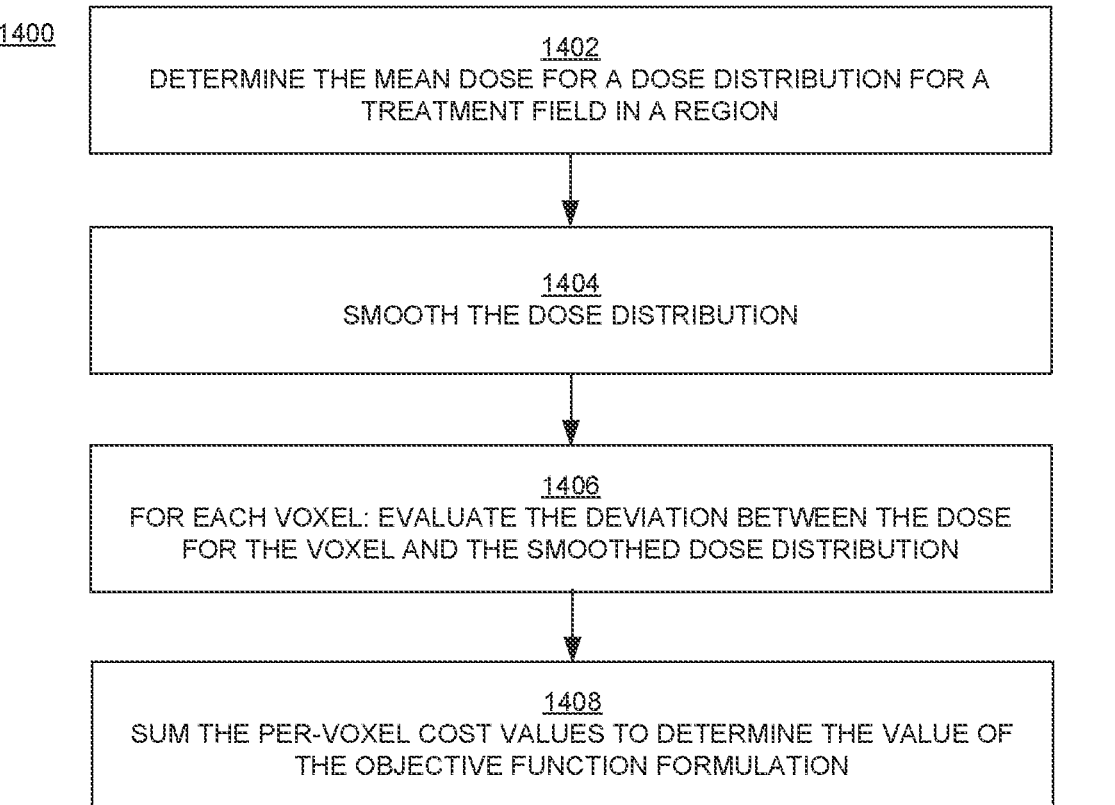

FIG. 14 is a flowchart 1400 of an example of a method for using the third objective function formulation (equation (4)) in embodiments according to the present disclosure. In block 1402, a respective dose value for each voxel in a treatment field in a region is determined using the dose distribution for that treatment field.

In block 1404, the dose distribution is smoothed. Smoothing techniques are known in the art, and the meaning of "smoothing" is known to persons of ordinary skill in the art.

In block 1406, for each voxel: deviation between the respective dose value for a voxel and the smoothed dose distribution is evaluated relative to a range associated with the dose distribution to determine a respective per-voxel value for the voxel, where the respective per-voxel value is non-zero (e.g., greater than zero) when deviation for the voxel is outside the range and is zero otherwise.

In block 1408, the per-voxel values are summed to determine the value of the fourth objective function formulation.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method for generating a radiation treatment plan, the computer-implemented method comprising:

generating a plurality of dose distributions for a region of a target volume, wherein each dose distribution of the plurality of dose distributions corresponds to a respective treatment field of a plurality of treatment fields that intersect the region;

determining a value of an objective function formulation, wherein the value of the objective function formulation is a function of a difference between a value that is based on a dose distribution of the plurality of dose distributions and a value for a range that is associated with the respective treatment field corresponding to the dose distribution, wherein the range is delineated by a first dose distribution and a second dose distribution; and using the value of the objective function formulation in a process for optimizing the radiation treatment plan.

2. The computer-implemented method of claim 1, wherein said determining a value of an objective function formulation comprises:

determining a mean dose for the dose distribution; and comparing the mean dose and the range, wherein the value of the objective function formulation is non-zero when the mean dose for the dose distribution is outside the range and is zero otherwise.

3. The computer-implemented method of claim 2, further comprising:

determining an average dose that is an average of the plurality of dose distributions; and defining the range using the average dose.

4. The computer-implemented method of claim 1, wherein said determining a value of an objective function formulation comprises:

determining a mean dose for the dose distribution;

determining a deviation of the dose distribution from the mean dose; and determining a difference between the deviation and the range, wherein the value of the objective function formulation is non-zero when the deviation is greater than the range and is zero otherwise.

5. The computer-implemented method of claim 1, wherein said determining a value of an objective function formulation comprises:

determining, with the dose distribution, a respective dose value for each voxel of a plurality of voxels in the respective treatment field;

determining a mean dose due to the respective treatment field;

for each voxel of the plurality of voxels, determining a difference between i) the range and ii) a difference between the respective dose value for a voxel of the plurality of voxels and the mean dose, to determine a respective per-voxel value for the voxel, wherein the respective per-voxel value is non-zero when the difference between the respective dose value for the voxel and the mean dose is greater than the range and is zero otherwise; and summing the respective per-voxel value for each voxel of the plurality of voxels to determine the value of the objective function formulation.

6. The computer-implemented method of claim 1, wherein said determining a value of an objective function formulation comprises:

determining, with the dose distribution, a respective dose value for each voxel of a plurality of voxels in a treatment field of the plurality of treatment fields;

smoothing the dose distribution to determine a smoothed dose distribution;

for each voxel of the plurality of voxels, determining a difference between i) the range and ii) a difference between the respective dose value for a voxel of the plurality of voxels and the smoothed dose distribution, to determine a respective per-voxel value for the voxel, wherein the respective per-voxel value is non-zero when the difference between the respective dose value for the voxel and the smoothed dose distribution is greater than the range and is zero otherwise; and summing the respective per-voxel value for each voxel of the plurality of voxels to determine the value of the objective function formulation.

7. The computer-implemented method of claim 1, further comprising:

selecting the objective function formulation from a plurality of objective function formulations, the plurality of objective function formulations including, an objective function formulation that is a function of an amount that a mean dose of a treatment field of the plurality of treatment fields is different from an average dose of a set of treatment fields of the plurality of treatment fields, within the region, an objective function formulation that is a function of a deviation of a dose of a treatment field of the plurality of treatment fields from a mean dose of the treatment field, within the region, an objective function formulation that is a function of a deviation of a dose of a treatment field of the plurality of treatment fields from a mean dose of the treatment field, on a per-voxel basis, within the region, and an objective function formulation that is a function of a deviation of a dose of a treatment field of the plurality of treatment fields from a smoothed dose of the treatment field, exceeding the range, on a per-voxel basis, within the region.

8. A non-transitory computer-readable storage medium having computer-executable instructions that, when executed, cause a computer system to perform a method for generating a plan for radiation treatment, the method comprising:

accessing, from a memory of the computer system, a radiation treatment plan including information describing a plurality of dose distributions for a region of a target volume, wherein each dose distribution of the plurality of dose distributions corresponds to a respective treatment field of a plurality of treatment fields that intersect the region;

accessing, from the memory, an objective function formulation that is a function of a difference between a value that is based on a dose distribution of the plurality of dose distributions and a value for a range that is associated with the respective treatment field corresponding to the dose distribution, wherein the range is delineated by a first dose distribution and a second dose distribution;

determining, based on the plurality of dose distributions, a value of the objective function formulation; and using the value of the objective function formulation in a process for optimizing the radiation treatment plan.

9. The non-transitory computer-readable storage medium of claim 8, wherein said determining a value of the objective function formulation comprises:

determining a mean dose for the dose distribution; and comparing the mean dose and the range, wherein the value of the objective function formulation is non-zero when the mean dose for the dose distribution is outside the range and is zero otherwise.

10. The non-transitory computer-readable storage medium of claim 9, wherein the method further comprises:

determining an average dose that is an average of the plurality of dose distributions; and defining the range associated with the dose distribution using the average dose.

11. The non-transitory computer-readable storage medium of claim 8, wherein said determining a value of the objective function formulation comprises:

determining a mean dose for the dose distribution;

determining a deviation of the dose distribution from the mean dose; and determining a difference between the deviation and the range, wherein the value of the objective function formulation is non-zero when the deviation is greater than the range and is zero otherwise.

12. The non-transitory computer-readable storage medium of claim 8, wherein said determining a value of the objective function formulation comprises:

determining, with the dose distribution, a respective dose value for each voxel of a plurality of voxels in the respective treatment field;

determining a mean dose due to the respective treatment field;

for each voxel of the plurality of voxels, determining a difference between i) the range and ii) a difference between the respective dose value for a voxel of the plurality of voxels and the mean dose, to determine a respective per-voxel value for the voxel, wherein the respective per-voxel value is non-zero when the difference between the respective dose value for the voxel and the mean dose is greater than the range and is zero otherwise; and summing the respective per-voxel value for each voxel of the plurality of voxels to determine the value of the objective function formulation.

13. The non-transitory computer-readable storage medium of claim 8, wherein said determining a value of the objective function formulation comprises:

determining, with the dose distribution, a respective dose value for each voxel of a plurality of voxels in a treatment field of the plurality of treatment fields;

smoothing the dose distribution to determine a smoothed dose distribution;

for each voxel of the plurality of voxels, determining a difference between i) the range and ii) a difference between the respective dose value for a voxel of the plurality of voxels and the smoothed dose distribution to determine a respective per-voxel value for the voxel, wherein the respective per-voxel value is non-zero when the difference between the respective dose value for the voxel and the smoothed dose distribution is greater than the range and is zero otherwise; and summing the respective per-voxel value for each voxel of the plurality of voxels to determine the value of the objective function formulation.

14. The non-transitory computer-readable storage medium of claim 8, wherein said accessing an objective function formulation comprises:

selecting one or more objective function formulations from a plurality of objective function formulations, the plurality of objective function formulations including, an objective function formulation that is a function of an amount that a mean dose of a treatment field of the plurality of treatment fields is different from an average dose of a set of treatment fields of the plurality of treatment fields, within the region, an objective function formulation that is a function of a deviation of a dose of a treatment field of the plurality of treatment fields from a mean dose of the treatment field, within the region, an objective function formulation that is a function of a deviation of a dose of a treatment field of the plurality of treatment fields from a mean dose of the treatment field, on a per-voxel basis, within the region, and an objective function formulation that is a function of a deviation of a dose of a treatment field of the plurality of treatment fields from a smoothed dose of the treatment field, exceeding a given range, on a per-voxel basis, within the region.

15. A computer system, comprising:

a processor; and memory coupled to the processor, the memory including instructions that, when executed, cause the processor to perform a method for planning radiation treatment, the method comprising:

determining a plurality of dose distributions, wherein each dose distribution of the plurality of dose distributions corresponds to a respective treatment field of a plurality of treatment fields;

determining a value of a cost function for each dose distribution of the plurality of dose distributions, wherein said determining a value of a cost function includes evaluating a value that is based on a dose distribution of the plurality of dose distributions against a value for a respective range associated with the dose distribution, wherein each respective range is delineated by a first dose distribution and a second dose distribution, and wherein the value of the cost function is non-zero when the dose distribution is outside the respective range and is zero otherwise; and using the value of the cost function for each dose distribution in a process for optimizing a radiation treatment plan.

16. The computer system of claim 15, wherein the method is performed for each region of a plurality of regions of a target volume.

17. The computer system of claim 15, wherein said evaluating comprises:

determining a mean dose for the dose distribution;

determining an average dose that is an average of the plurality of dose distributions;

defining the respective range associated with the dose distribution using the average dose; and comparing the mean dose and the respective range, wherein the value of the cost function is non-zero when the mean dose for the dose distribution is outside the respective range and is zero otherwise.

18. The computer system of claim 15, wherein said evaluating comprises:

determining a mean dose for the dose distribution;

determining a deviation of the dose distribution from the mean dose; and determining a difference between the deviation and the respective range, wherein the value of the cost function is non-zero when the deviation is greater than the respective range and is zero otherwise.

19. The computer system of claim 15, wherein said evaluating comprises:

determining, with the dose distribution, a respective dose value for each voxel of a plurality of voxels in a treatment field of the plurality of treatment fields;

determining a mean dose due to the treatment field;

for each voxel of the plurality of voxels, evaluating determining a difference between i) the respective range and ii) a difference between the respective dose value for a voxel of the plurality of voxels and the mean dose, to determine a respective per-voxel value for the voxel, wherein the respective per-voxel value is non-zero when the difference between the respective dose value for the voxel and the mean dose is greater than the respective range and is zero otherwise; and summing the respective per-voxel value for each voxel of the plurality of voxels to determine the value of the cost function.

20. The computer system of claim 15, wherein said evaluating comprises:

determining, with the dose distribution, a respective dose value for each voxel of a plurality of voxels in a treatment field of the plurality of treatment fields;

smoothing the dose distribution to determine a smoothed dose distribution;

for each voxel of the plurality of voxels, determining a difference between i) the respective range and ii) a difference between the respective dose value for a voxel of the plurality of voxels and the smoothed dose distribution to determine a respective per-voxel value for the voxel, wherein the respective per-voxel value is non-zero when the difference between the respective dose value for the voxel and the smoothed dose distribution is greater than the respective range and is zero otherwise; and summing the respective per-voxel value for each voxel of the plurality of voxels to determine the value of the cost function.

21. The computer-implemented method of claim 1, further comprising:

selecting the objective function formulation from a plurality of objective function formulations.

* * * * *